(12) United States Patent
Painchaud et al.

(10) Patent No.: US 11,426,572 B2
(45) Date of Patent: Aug. 30, 2022

(54) IMPLANT INJECTION DEVICE PROVIDED WITH FRICTIONAL RETAINING MEANS

(71) Applicant: Nemera La Verpillière, La Verpilliere (FR)

(72) Inventors: Gaëtan Painchaud, Francheville (FR); Pascal Dugand, Estrablin (FR); Thomas Megard, La Roche-Vineuse (FR)

(73) Assignee: Nemera La Verpillière

( * ) Notice: Subject to any disclaimer, the term of this patent is extended or adjusted under 35 U.S.C. 154(b) by 507 days.

(21) Appl. No.: 16/388,301

(22) Filed: Apr. 18, 2019

(65) Prior Publication Data
US 2019/0321615 A1   Oct. 24, 2019

(30) Foreign Application Priority Data

Apr. 18, 2018  (FR) ...................... 1853404

(51) Int. Cl.
*A61M 37/00* (2006.01)
*A61B 17/34* (2006.01)

(52) U.S. Cl.
CPC ..... *A61M 37/0069* (2013.01); *A61B 17/3468* (2013.01)

(58) Field of Classification Search
CPC ............ A61M 37/0069; A61M 31/007; A61M 31/00; A61M 2202/06; A61M 2210/04; A61B 17/3468; A61B 2090/3987; A61B 17/34; A61B 17/3462; A61B 2017/347; A61D 7/00; A61F 9/0017; A61F 9/0008; A61F 9/0026; A61F 2/1672; A61K 9/02
See application file for complete search history.

(56) References Cited

U.S. PATENT DOCUMENTS

| | | | | |
|---|---|---|---|---|
| 5,284,479 | A | * | 2/1994 | de Jong ............ A61M 37/0069 604/130 |
| 5,858,006 | A | * | 1/1999 | Van der AA ....... A61M 5/3286 604/239 |
| 2005/0101967 | A1 | * | 5/2005 | Weber ............... A61M 37/0069 606/107 |
| 2006/0282042 | A1 | | 12/2006 | Walters et al. |
| 2009/0281520 | A1 | | 11/2009 | Highley et al. |

(Continued)

FOREIGN PATENT DOCUMENTS

| | | |
|---|---|---|
| EP | 0531036 A1 | 3/1993 |
| EP | 2335771 A1 | 6/2011 |

(Continued)

*Primary Examiner* — Deanna K Hall
*Assistant Examiner* — Alexandra Lalonde
(74) *Attorney, Agent, or Firm* — St. Onge Steward Johnston & Reens LLC

(57) ABSTRACT

An implant injection device, includes an injection needle, a receiver housing for receiving at least one implant, injection device, including a pushing rod, arranged upstream from the implant housed in the receiver housing, and configured to push the implant through the injection needle between an initial position and a final position, a pushing member for pushing the pushing rod between the initial position and the final position, a retaining member for retaining the pushing rod by friction relative to the injection needle, opposing the displacement of the pushing rod to its final position, it being possible for a user to actuate the retaining member.

8 Claims, 5 Drawing Sheets

(56) References Cited

U.S. PATENT DOCUMENTS

| | | | |
|---|---|---|---|
| 2010/0256555 A1* | 10/2010 | Birmelin | A61M 37/0069 |
| | | | 604/60 |
| 2013/0267931 A1 | 10/2013 | Nazzaro et al. | |
| 2014/0100584 A1* | 4/2014 | Konstorum | A61B 17/3468 |
| | | | 606/109 |
| 2015/0038905 A1* | 2/2015 | Andino | A61M 5/2033 |
| | | | 604/117 |
| 2015/0105719 A1* | 4/2015 | Haindl | A61B 17/3468 |
| | | | 604/60 |
| 2019/0298512 A1* | 10/2019 | Muchhala | A61F 2/1662 |

FOREIGN PATENT DOCUMENTS

| | | | |
|---|---|---|---|
| WO | 2004026106 A2 | 4/2004 | |
| WO | 2006071554 A2 | 7/2006 | |

* cited by examiner

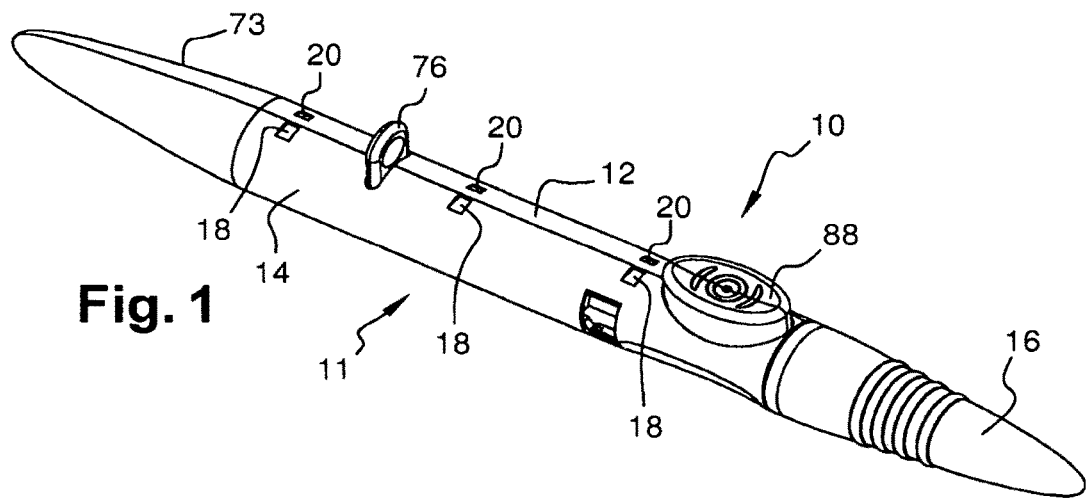
Fig. 1
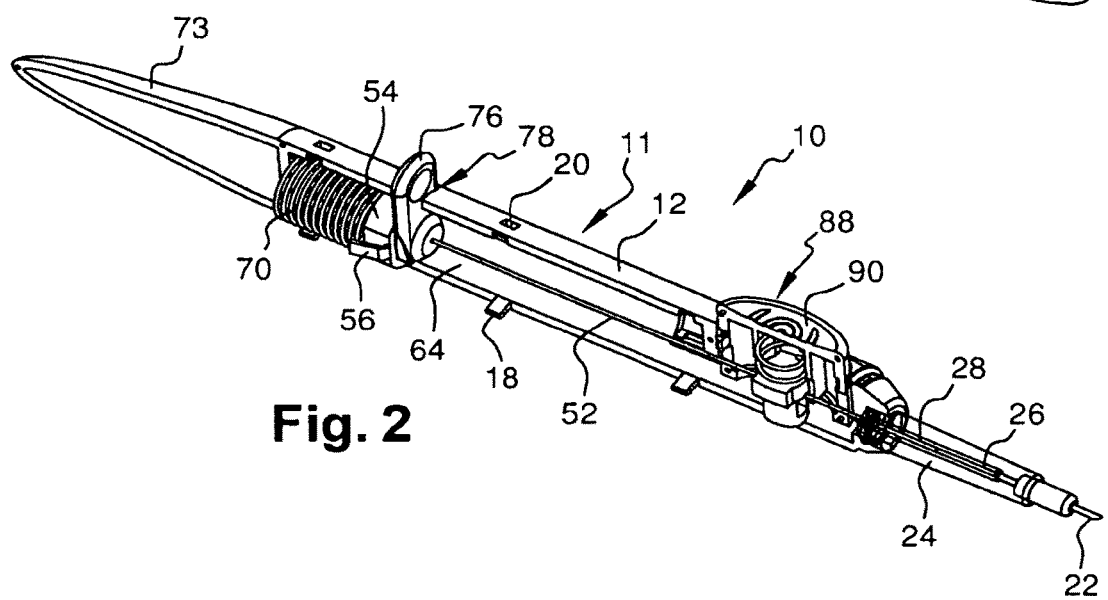
Fig. 2
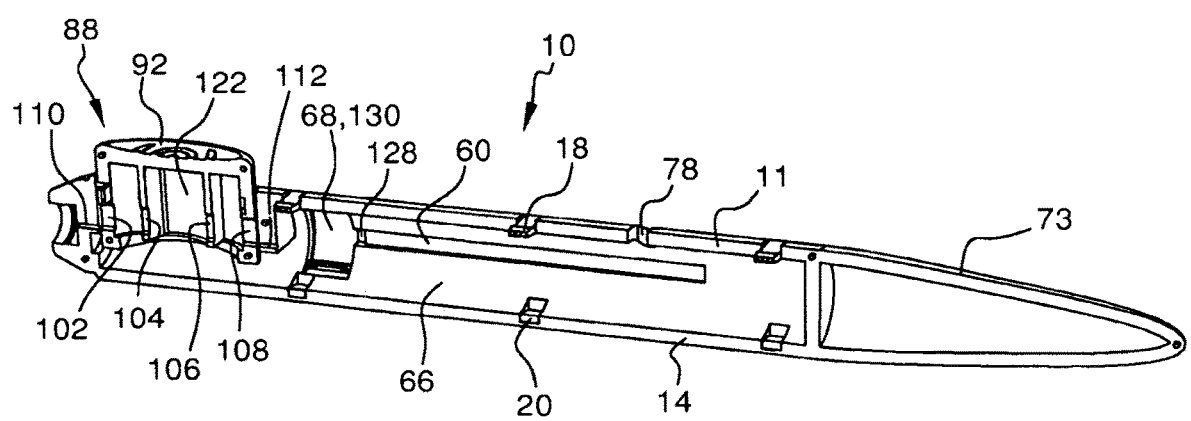
Fig. 2bis

IMPLANT INJECTION DEVICE PROVIDED WITH FRICTIONAL RETAINING MEANS

FIELD OF THE INVENTION

The invention relates to the technical field of injecting one or more implants into a patient's body.

BACKGROUND OF THE INVENTION

Implant injection devices, comprising a hollow needle attached to a housing receiving an implant, are known. The implant is injected using a pushing rod, which pushes the implant through the hollow needle then beyond to inject the implant into a patient's body.

In particular, document US20090281520A1 describes an implant injection device in which the implant can be injected by slidably pressing a button, the button then being pressed by the user in a direction substantially parallel to the injection direction. Thus, before actuation, the pushing rod is retracted and the button is located on the side of the proximal end of the device, in other words the end opposite the injection end. When the user slidably presses the button, the button slides in a direction substantially parallel to the injection direction and moves the pushing rod, which pushes the implant and allows its injection.

However, with such actuation by slidably pressing, the user cannot inject very long implants or several implants easily. This actuation is generally carried out by the user's thumb, which has a limited actuation stroke. In addition, with such actuation, good injection accuracy cannot be maintained over a long stroke. The risk of unwanted movement in a direction substantially parallel to the injection direction is in fact higher when the actuation length increases, which is not desirable to guarantee correct injection, in particular concerning the depth of injection into the patient's body, and to avoid breaking the implant or injuring the patient.

Thus, in view of their actuation type, these implant injection devices cannot be used to easily inject a very long implant or a plurality of implants.

SUMMARY OF THE INVENTION

This invention aims in particular to provide an implant injection device which can be used to easily inject a very long implant and/or a plurality of implants.

Thus, the invention relates in particular to a device for injecting an implant comprising:
an injection needle,
a receiver housing for receiving at least one implant,
injection means, comprising:
a pushing rod, arranged upstream from the implant housed in the receiver housing, and configured to push the implant through the injection needle between an initial position and a final position,
means for pushing the pushing rod between the initial position and the final position,
means for retaining the pushing rod by friction relative to the injection needle, opposing the displacement of the pushing rod to its final position, it being possible for a user to actuate the retaining means.

Thus, it is proposed to perform the injection by using pushing means to simplify the displacement of the pushing rod, and also by making the user adjust the retention of the pushing rod rather than by asking the user to actuate the pushing rod over a relatively long distance. In other words, by combining the use of pushing means and frictional retaining means, the movement to be made by the user to inject the implant is in particular of small amplitude, in order to increase the size and/or number of implants that can be injected once the needle is inserted into the patient's body. In other words, the user controls easily, and as required, the thrust exerted on the pushing rod via the actuatable retaining means. In addition, frictional retaining means are different from a stop. Thus, for example, means for retaining the pushing rod by friction retain the pushing rod solely by friction of the retaining means on the pushing rod. In other words, the frictional retaining means only exert frictional forces on the pushing rod, opposing the displacement of the pushing rod relative to the frictional retaining means.

An "implant" is preferably understood to mean a pharmaceutical compound in solid or semi-solid state, for example in the form of an encapsulated liquid and/or an electronic component, for example an RFID type electronic chip. A "patient" or "subject" is generally understood to mean a living being, for example a mammal, in particular a human being. The user is generally a person different from the patient but the user may be the patient himself.

In this description, it is understood that the distal direction designates the direction farthest away from a user's fingers, in other words closest to the skin or the surface of a patient at the time of an injection, and the proximal direction designates the direction opposite to the distal direction. In other words, it is considered that the distal direction and the distal sense are the direction and sense which go towards the "front" of the implant injection device, also called the injection direction. In particular, the distal end of a part corresponds to the end located on the side of the injection needle and the proximal end corresponds to the opposite end. It is also understood that the injection axis, which is the injection direction, corresponds to the axis of the implant injection device defined by the axis of the injection needle.

Consequently, it is understood that the "downstream" direction is a direction opposite to the "upstream" direction and corresponds to the direction towards the distal end of the implant injection device, in other words towards the injection site, towards the end configured to be in contact with the implant injection site. Thus, the "downstream" direction may also be called the injection direction. It is understood that the terms "upstream" and "downstream" designate the distal and proximal directions, a downstream element being arranged further away in the distal direction than an upstream element.

The implant injection device may further comprise one or more of the following characteristics, taken alone or in combination.

The retaining means comprise:
an actuation button comprising a first bearing surface intended to be in contact with the pushing rod,
a bearing support comprising a second bearing surface intended to be in contact with the pushing rod,
the actuation button being movable relative to the bearing support between a retaining position, in which the first and second bearing surfaces each exert a first retaining force on the pushing rod, and a release position during actuation by a user of the actuation button, in which the bearing surfaces each exert a second retaining force less than the first retaining force on the pushing rod, the second retaining forces allowing the displacement of the pushing rod towards the distal direction relative to the injection needle. Thus, actuation by a user is particularly easy, due to the fact that by simply actuating the actuation button, the retention exerted by the first and second bearing surfaces on the pushing rod is reduced, and the pushing means are therefore allowed to displace the pushing rod.

At least one of the second retaining forces is zero. In other words, in the position in which the actuation button is released, there is no more or substantially no more contact between the first bearing surface and the pushing rod and/or between the second bearing surface and the pushing rod.

The bearing support is carried by a unit or is formed by a unit.

The injection needle is attached to a unit of the implant injection device, the unit further being able to carry the receiver housing and the injection means. The unit is preferably an external unit, allowing the implant injection device to be gripped. For example, the injection needle is attached to the unit. Thus, when the implant injection device is used by a user, the injection needle remains in a fixed position relative to the unit. In particular, it does not retract either when injecting the at least one implant or after injecting the at least one implant. Consequently, this simplifies the design of the implant injection device.

The retaining means comprise means for returning the actuation button to its retaining position, in particular a return spring. Thus, actuation by the user is more pleasant and more precise, since the user simply needs to stop pressing the actuation button to stop the displacement of the pushing rod, therefore to make a pause during the injection. This allows the user, for example, to change the direction of the injection needle to inject another implant beside the first implant and not inject the two implants one behind the other.

The implant injection device comprises an element for controlling the pushing rod, slidably mounted relative to a unit, the unit and the control element being provided with means for guiding in translation the control element relative to the unit. Thus, the pushing rod is positioned and guided during its displacement more precisely. Advantageously, the control element comprises a sliding bush provided with a lug cooperating with a groove carried by a unit and/or provided with a groove cooperating with a lug carried by a unit.

The pushing means are automatic. Thus, a user does not have to exert a pushing force in a distal direction on the pushing rod, which improves the actuation precision when the user actuates the means for retaining the pushing rod. Consequently, this improves the precision of the injection process.

The pushing means comprise a thrust spring, resting between a unit and the pushing rod. The thrust spring can work in traction or in compression. Using a thrust spring to exert the thrust on the pushing rod is particularly interesting since the force of the thrust spring makes the injection easier and more precise, while being controlled by the retaining means to allow the user to control the injection. This is particularly advantageous to inject a long implant or a plurality of implants. The maximum force exerted on the pushing rod is defined so as to avoid damaging the pushing rod and/or an implant and to simplify the actuation of the retaining means by a user. In fact, the lower the force to be exerted by the thrust spring, the lower the force to be exerted by the retaining means to retain the pushing rod.

The implant injection device comprises a retractable locking element for blocking the pushing means, configured, in a locking configuration, to hold the implant injection device in the initial position and, in a retracted configuration, to allow the implant injection device to move to its final position. Thus, the transport and handling of the implant injection device before its use are safer, since the implant injection device cannot be actuated accidentally or by being dropped.

The implant injection device comprises locking means arranged to block the pushing rod in its final position. Thus, the implant injection device is not reusable, thereby respecting hygiene constraints relating to this type of implant injection device.

The pushing rod is configured to push at least one implant through the injection needle between a proximal initial position and a distal final position in which at least one implant is injected. Thus, when the implant injection device is used by a user, the pushing rod is only displaced in the distal direction between the initial position and the final position.

In its final position, the pushing rod projects towards the distal direction past the end of the injection needle. Thus, the pushing rod forms in this case a safety element for the end of the injection needle which may be beveled for easier insertion into the skin. The pushing rod can then prevent the needle from exerting its insertion function, for example on a person or an object if the implant injection device is dropped. Thus, if the implant injection device is dropped or pressed in the distal direction, the contact with the implant injection device is made via the pushing rod and not with the end of the injection needle.

The retaining means comprise a pad carried by a unit, comprising a third bearing surface intended to be in contact with the pushing rod to create an additional retaining force on the pushing rod. Thus, the distribution of the radial forces exerted on the pushing rod is improved, which avoids its deformation and simplifies actuation by the user.

The actuation button may be a button to press or a laterally actuated button, pivotally mounted about an axis substantially orthogonal to the injection axis. These types of actuation are particularly easy to use.

The retaining means comprise a pad, return means being arranged between the actuation button and the pad. In particular, this simplifies actuation, which is more pleasant for a user.

The means for returning the actuation button comprise a return spring working in traction or compression.

The retaining means are continuously adjustable, so as to be able to vary the pushing rod displacement speed manually under the action of the pushing means. Thus, it is proposed not only to retain the displacement of the pushing rod, but it is further proposed to be able to adjust this retention continuously, so that the retaining force varies gradually, without jerks and to adapt the degree of retention to requirements, unlike retaining means which would only be configured to perform a complete retention or no retention at all. In other words, the retaining means can be actuated by a user, irrespective of the position of the pushing rod between its initial position and its final position.

The implant injection device comprises a unit carrying the second bearing surface, the second bearing surface being in particular made in one piece with the unit.

The thrust spring is arranged between the unit and the sliding bush.

The locking means comprise a bracket carried by a sliding bush cooperating with a recess carried by a unit.

The retaining means are actuated by a ramp provided on the actuation button or on the unit. Thus, the ramp simplifies the gradual control of the retaining force which allows a more or less pronounced permanent contact depending on how the user presses the actuation button.

BRIEF DESCRIPTION OF THE DRAWINGS

It will be easier to understand the invention on reading the description below, given as an example and referring to the drawings, on which:

FIG. 1 is a perspective view of an implant injection device according to one embodiment, in storage configuration before injection;

FIG. 2 is a side and perspective view of a part of the implant injection device of FIG. 1, in which the pushing rod is in an initial position;

FIG. 2bis is a side and perspective view of a complementary part of the implant injection device not shown on FIG. 2 and illustrated with the distal part pointing to the left;

DETAILED DESCRIPTION OF THE INVENTION

Figure 3:
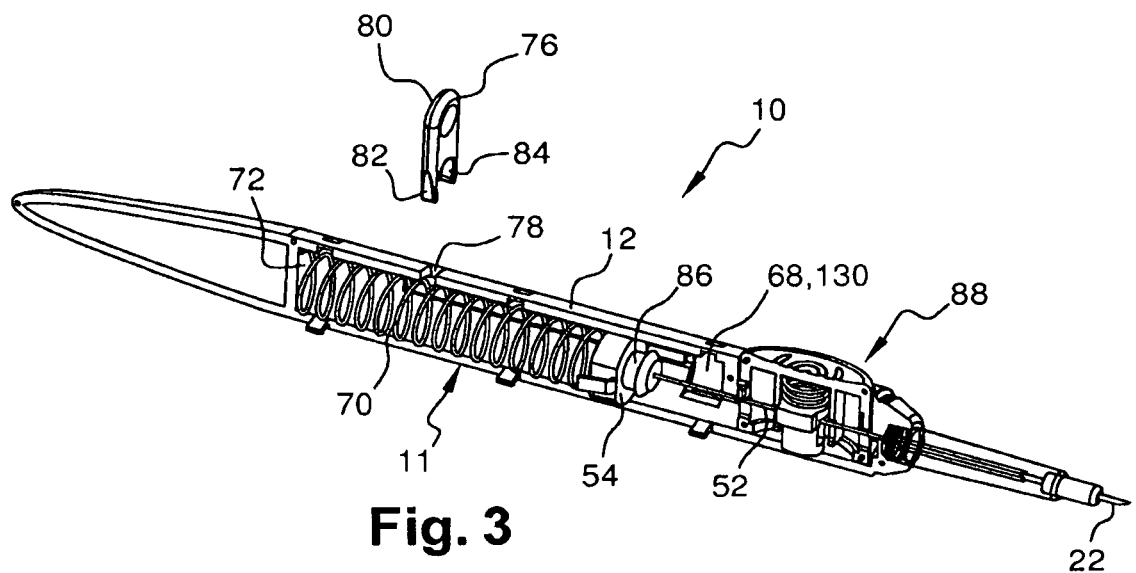
FIG. 3 is a view similar to FIG. 2, the retractable locking element being retracted, the pushing rod being in an intermediate position.

As shown on the figures, an implant injection device 10 is configured to inject one or more implants into a patient's body.

As shown on FIG. 1, the implant injection device 10 comprises a unit 11. In this case, the unit 11 is an external gripping unit, carrying a surface for a user to grip the implant injection device 10. In this example, it consists of two-half units 12, 14. The unit 11 also carries a removable cap.

Each half-unit 12, 14 comprises assembly means, for example brackets 18 and housings 20 intended to receive, in the state assembled by clipping, the brackets 18 of the other half-unit 14, 12.

The cap 16 is a cap protecting the injection needle, in this case it is assembled on the unit 11 by clipping, or by any other suitable means, for example by screwing. In this example, the cap 16 is bullet-shaped, provided locally with reliefs for easier gripping. In the state assembled on the unit 11, the cap 16 surrounds an injection needle 22 (shown on FIG. 2) connected to a receiver housing 24 (shown on FIG. 2) for receiving at least one implant. Preferably, the implant injection device 10 illustrated is configured to inject two implants into a patient's body, in particular two implants 26, 28 (shown on FIG. 2). The cap 16 is removable, so as to release the injection needle 22. Thus, once the cap 16 has been removed, the injection needle 22 can be inserted into a patient's body to inject implants 26, 28 into the patient's body.

Figure 5:
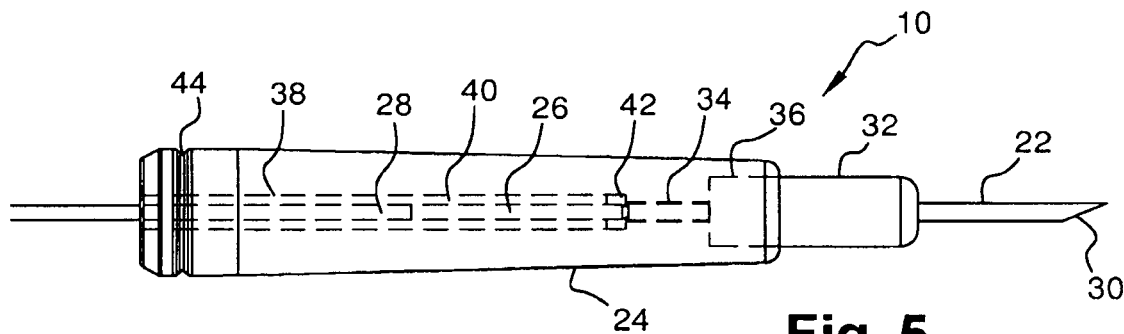
FIG. 5 is a view of the receiver housing and of the injection needle of the implant injection device of FIG. 2.

The injection needle 22 is hollow and is for example made of metal such as stainless steel. As shown on the figures and in particular on FIG. 5, the injection needle 22 may comprise a beveled distal end 30 for easier insertion into the patient's body. The injection needle 22 may further be carried by a support element 32, which can be made of plastic and is intended to limit the depth of insertion of the injection needle 22 into the patient's body.

In this case, the receiver housing 24 is attached to the unit 11. Alternatively, it could be formed directly in the unit 11, being made in one piece with it. In this example, the receiver housing 24 is made of transparent plastic. Thus, a user can detect visually the presence of the implants 26, 28 in the implant injection device 10, before performing the injection, when the cap 16 is removed. Alternatively, a hole could be made in the receiver housing 24.

The receiver housing 24 is arranged upstream from the injection needle 22, and is intended to receive the implants 26, 28 such that the implants 26, 28 are arranged upstream from the injection needle 22, in the injection direction of the injection needle 22.

The receiver housing 24 consists for example of a cylinder, of slightly frustoconical shape. Thus, as shown on FIG. 5, the receiver housing 24 is hollow and comprises at its distal end a section 34 having an inner diameter corresponding substantially to the outer diameter of the injection needle. Thus, the injection needle 22 can be inserted into the section 34. The receiver housing 24 may further comprise a bore 36 intended to house a part of the support element 32. This stiffens the assembly formed by the receiver housing 24, the injection needle 22 and the support element 32.

The receiver housing 24 may also comprise a bore 38 intended to house a receiving member 40, which may contain the implants 26, 28. The receiving member 40 may consist of a tube, made in particular of transparent plastic. Thus, it can contain the implants 26, 28. For example, if the receiving member 40 contains two implants 26, 28, the two implants 26, 28 are arranged one behind the other, in other words one upstream from the other, in the injection direction. The receiving member 40 may comprise a distal end 42 provided with an implant retaining means, such as a membrane or a slight narrowing of its inner diameter, intended to prevent an implant from falling through the injection needle 22, for example under the effect of the force of gravity. The distal end 42 may alternatively comprise a flexible element for retaining the implant 26, 28 comprising an orifice of diameter less than that of the implant 26, 28, the orifice being configured to deform and allow the implant 26, 28 to pass towards the injection needle 22 during the injection.

Figure 7:
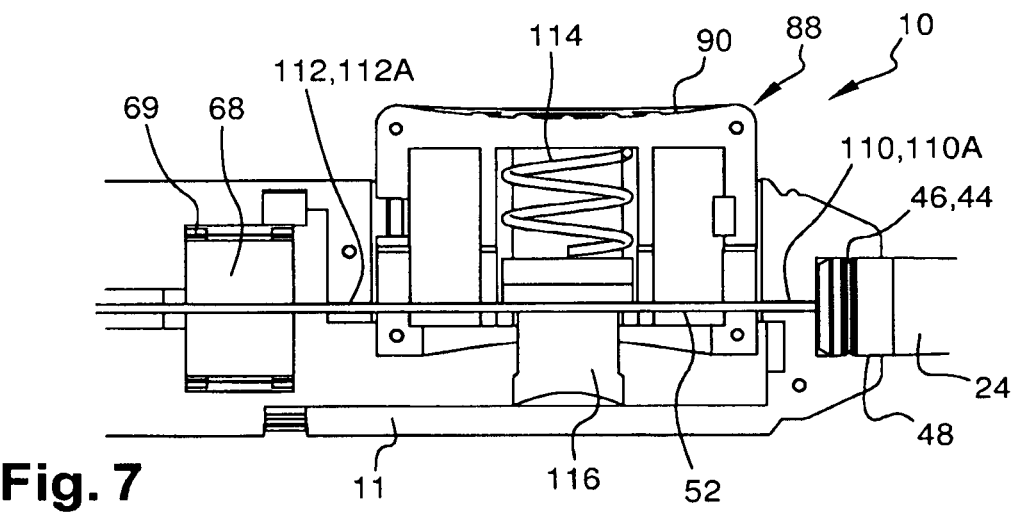
FIG. 7 is a side view of a part of the implant injection device shown on FIG. 6.

Lastly in this example, as shown on FIG. 7, the receiver housing 24 comprises a proximal end having a clipping element, such as for example a peripheral groove 44. Thus, the receiver housing 24 is attached to the unit 11, the unit 11 comprising a complementary clipping element, such as for example a peripheral protrusion 46 formed in a bore 48, the peripheral protrusion 46 cooperating with the peripheral clipping groove 44, shown on FIG. 7.

In order to inject the implants 26, 28, the implant injection device 10 comprises injection means. In this case, these injection means are arranged in the unit 11.

As shown on FIG. 2, the injection means comprise a pushing rod 52, means for pushing the pushing rod 52 and means for retaining the pushing rod 52 by friction.

The pushing rod 52 can be made of metal, for example steel, preferably stainless steel. The pushing rod 52 is arranged upstream from an implant, for example upstream from the implant 28 which is itself the implant being arranged in the most upstream position of the implants 26, 28. The pushing rod 52 is therefore configured to push the implant, for example the implants 26, 28, through the injection needle 22 between an initial position and a final position. Thus, in the initial position of the pushing rod 52, the implants 26, 28 are housed in the receiver housing 24, and in the final position of the pushing rod 52, the implants 26, 28 have passed through the injection needle 22 and are a priori placed in a patient's body.

Figure 10:
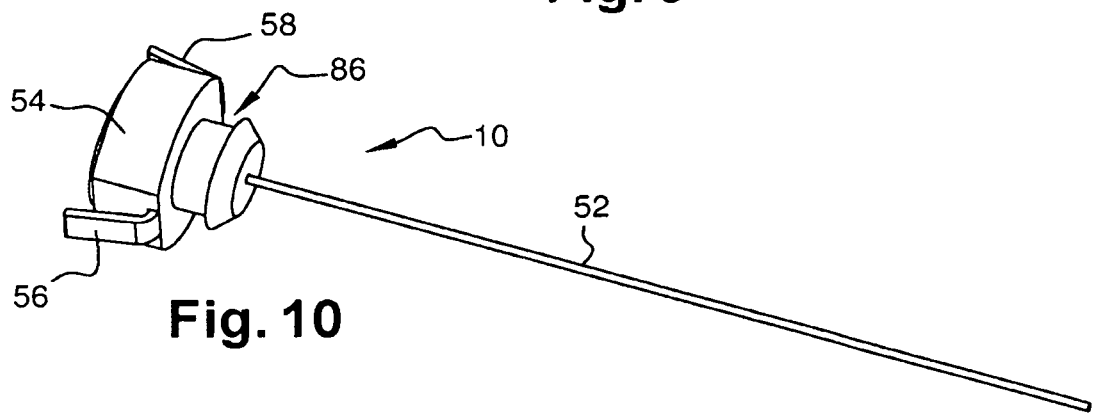
FIG. 10 is a perspective view of a detail of the implant injection device of FIG. 1.

In this case, the implant injection device 10 further comprises an element 54 for controlling the pushing rod 52, slidably mounted relative to the unit 11. The control element 54 comprises a sliding bush provided with a lug cooperating with a groove carried by the unit 11 and/or provided with a groove cooperating with a lug carried by the unit 11. More precisely, the control element 54 is attached to the pushing rod 52 and is formed by the sliding bush, as shown in particular on FIG. 10. The control element 54 and the unit 11 comprise means for guiding in translation the control element 54 relative to the unit 11. The means for guiding in translation comprise for example a lug, or a bracket 56, 58, carried by the control element 54, and a groove 60, 62 (shown on FIG. 2bis) opposite the lug or the bracket 56, 58 and made on an inner wall of the unit 11, so as to cooperate with the lug or the bracket 56, 58. In particular the control element 54 comprises two brackets 56, 58, each opposite a groove 60, 62 made on an inner wall 64, 66 of a respective half-unit 12, 14.

According to another embodiment not shown, the unit may comprise a rib and the control element a groove adapted to receive the rib, the rib and the groove acting as lug and groove whose elements carrying them are reversed.

The means for guiding in translation are shaped to guide to control element 54 and the pushing rod 52 in translation in the injection direction of the injection needle 22.

The unit 11 may comprise an opening, in particular an opening 130 on each half-unit 12, 14. Each opening 130 can be closed by a cover 68 shown on FIG. 2bis, which can be attached by clipping to the unit 11, in particular to each half-unit 12, 14. Thus, the cover 68 comprises a plurality of brackets 69, shown on FIG. 6, in particular four brackets 69, which cooperate with the grooves to attach the cover 68 to the unit 11, in particular to each half-unit 12, 14. For example, the cover 68 is made of transparent plastic. Advantageously, the cover 68 can be placed at the control element 54, when the pushing rod 52 is in a final position. Thus, a user can detect visually that the implant injection device 10 has reached a final injection position. The cover 68 may also have a shape corresponding to that of the unit 11, in particular its outside may be flush with the unit 11 when it is fitted on the unit 11.

The unit 11 further comprises a through window 132 receiving an actuation button described below.

In this example, the means for pushing the pushing rod 52 comprise a thrust spring 70 (shown on FIGS. 3 and 4), resting between the unit 11 and the pushing rod 52. In particular, the thrust spring 70 is a spring working in compression. Alternatively, the thrust spring can be a spring working in traction. For example, the thrust spring 70 rests on the side of the unit 11 on an inner stop 72 formed by a substantially flat surface on the unit 11. As shown in particular on FIG. 3, the inner stop 72 can be formed partially on each half-unit 12, 14. In addition, the thrust spring 70 rests on the side of the pushing rod 52 on a stop formed by a substantially flat surface on the control element 54, this stop being opposite the inner stop 72 formed on the unit 11. In particular, the thrust spring 70 is arranged between the unit 11 and the sliding bush 54.

As shown in particular on FIG. 2, the unit 11 is, at its end 73 opposite to the injection direction, bullet-shaped for easier gripping. An advantage of the implant injection device 10 is that it can be used with a single hand. In particular, the unit 11 can be bullet-shaped past the inner stop 72, in the direction opposite to the injection direction.

The force supplied by the thrust spring 70 is transmitted to the pushing rod 52 via the control element 54. The pushing rod 52 can then exert a force to inject an implant, in particular implants 26, 28, into a patient's body. Thus, the thrust spring 70 is configured to push the pushing rode 52 from its initial position to its final position.

The implant injection device 10 may further comprise a retractable locking element 76 for locking the pushing means, shown in particular on FIGS. 2 and 3. When in locking configuration, the retractable locking element 76 prevents the pushing means from accidentally displacing the pushing rod 52, in particular during the transport or storage of the implant injection device 10. For example, the retractable locking element consists of a key 76. When in retracted configuration, the retractable locking element 76 allows the displacement of the pushing rod 52.

In the initial position of the pushing rod, as shown on FIG. 2, the key 76 is inserted in an orifice 78 formed in the unit 11, in particular in a complementary manner on each half-unit 12, 14. As shown on FIG. 3, one end of the key 76 consists of a gripping end 80. The other end consists for example of two branches 82, 84, which are configured to engage in a peripheral groove 86 (shown on FIG. 10) formed on the control element 54, in particular on the sliding bush. Thus, the control element 54 is prevented from moving in the injection direction, the forces being transmitted from the pushing means to the control element 54, then from the control element 54 to the key 76, and from the key 76 to the unit 11 at the walls of the orifice 78. Thus, the key 76 must be removed before using the implant injection device 10 to inject an implant 26, 28 into a patient's body.

The means for retaining the pushing rod 52 by friction are configured to retain the pushing rod 52 relative to the injection needle 22 and to the unit 11. These retaining means oppose the displacement of the pushing rod 52 towards its final position and therefore the injection of the implants 26, 28. These retaining means can be actuated by a user.

The retaining means comprise for example an actuation button 88.

The actuation button 88 projects partially outside the unit 11 through the through window 132 to allow actuation by a user, in particular by pressing. It may consist of two half-buttons 90, 92, shown on FIGS. 2 and 2bis. Each half-button 90, 92 comprises assembly means, in this case a bracket 94 and a housing 96 (shown on FIG. 6), intended to receive, in the state assembled by clipping, the bracket 94 of the other half-button 92, 90. Each half-button 90, 92 may further comprise positioning pins 98 and positioning holes 100 (also shown on FIG. 6), intended to receive, in the assembled state of the actuation button 88, the positioning pins of the other half-button 92, 90.

In the example shown in particular on FIGS. 1 and 2, 6 and 7, the actuation button 88 is crossed by the pushing rod 52, which passes through holes formed by respective grooves 102, 104, 106, 108 made on each half-button 90, 92, arranged opposite so as to form holes when taken two at a time, these holes being aligned axially together. Although several holes are thus formed on the example shown, in particular two or four holes, a single hole can be formed in the actuation button, the hole being crossed by the pushing rod.

The actuation button 88 comprises a first bearing surface intended to be in contact with the pushing rod 52, in particular when the retaining means are not actuated by the user. The bearing surface consists of the wall of one of the holes formed by the grooves 102, 104, 106, 108. For example, the actuation button 88 may comprise four first bearing surfaces 102A, 104A, 106A, 108A located on an edge of the grooves 102, 104, 106, 108. This edge of each of these grooves 102, 104, 106, 108 may be the lower edge, which is opposite the upper edge of these grooves 102, 104, 106, 108 which is closer to the part of the actuation button 88 projecting outside the unit 11 than the lower edge.

Figure 6:
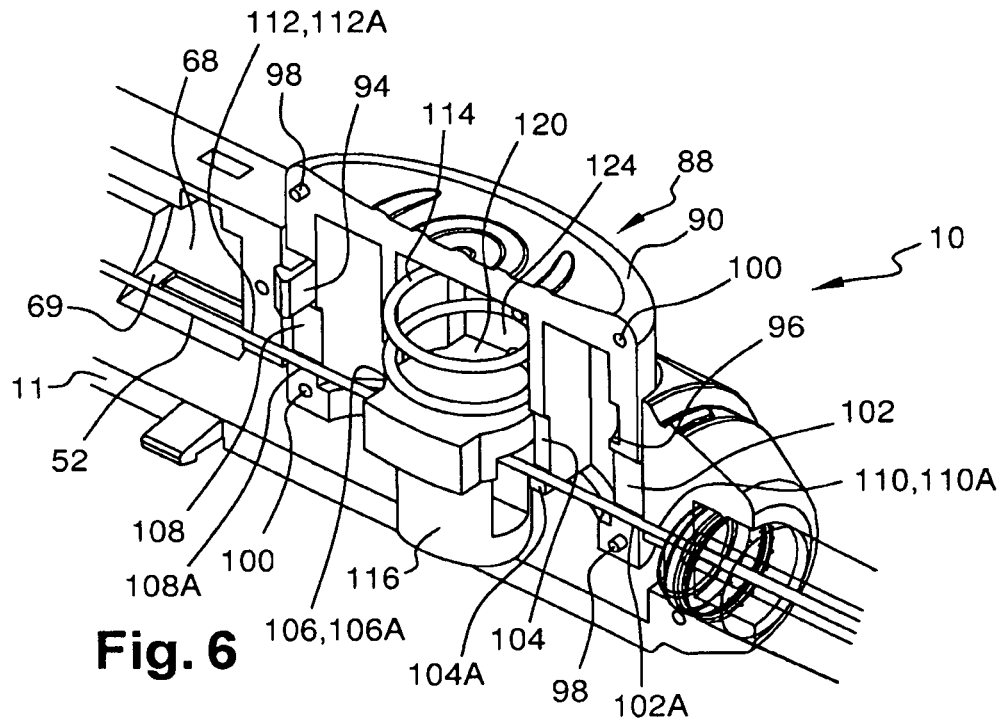
FIG. 6 is an enlarged view of a part of FIG. 2.
Figure 14:
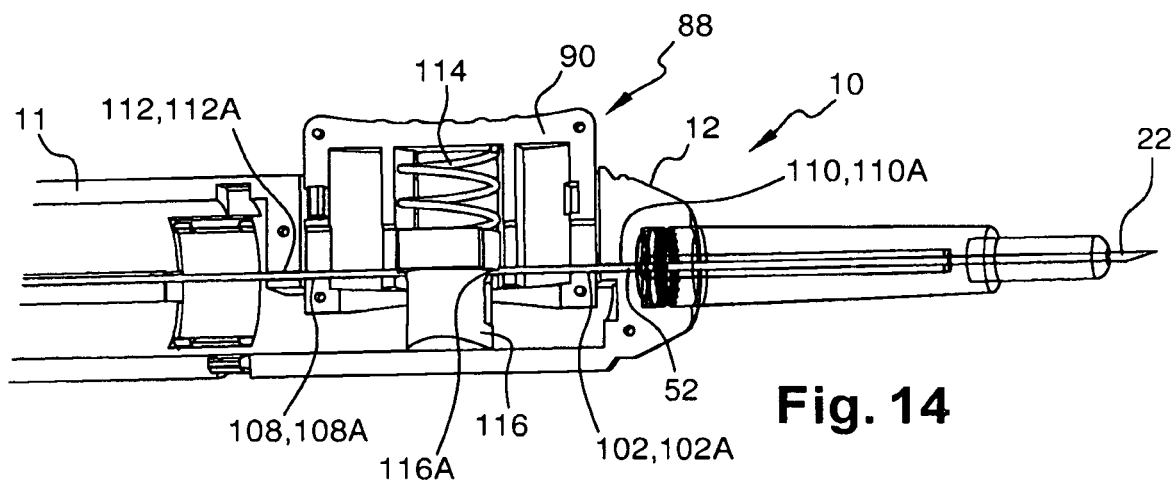
FIG. 14 is a cross-sectional and perspective view of a part of the implant injection device of FIG. 12.

The retaining means further comprise a bearing support 110, 112, 116, shown for example on FIGS. 6 and 14. The bearing support 110, 112, 116 comprises a second bearing surface 110A, 112A intended to be in contact with the pushing rod 52, in particular when the retaining means are not actuated by the user. In the example shown, the bearing surface is at least partially formed by the parts 110, 112 of the unit 11. In other words, the second bearing surface 110A, 112A comprises a surface carried by the unit 11. In particular, the second bearing surface 110A, 112A comprises internal surfaces of guide holes 110, 112 for guiding the pushing rod 52, the guide holes 110, 112 being formed in the unit 11. Thus, in this case, the second bearing surface 110A, 112A is formed by the unit 11, the second bearing surface 110A, 112A being made in one piece with the unit 11. The bearing support 110, 112, 116 may possibly also comprise a pad 116, as described below.

The actuation button 88 is movable relative to the bearing support 110, 112, 116 between a retaining position and a release position when a user actuates the actuation button 88. In the retaining position, the first and second bearing surfaces 102A, 104A, 106A, 108A, 110A, 112A each exert a first retaining force on the pushing rod 52. In the release position, the first and second bearing surfaces 102A, 104A, 106A, 108A, 110A, 112A each exert a second retaining force less than the first retaining force on the pushing rod 52. The second retaining forces therefore allow the displacement of the pushing rod 52 towards the distal direction relative to the injection needle 22, in other words in the injection direction. At least one of the second retaining forces can be zero. In this case, there may no longer be any contact between the pushing rod 52 and one of the first and second bearing surfaces 102A, 104A, 106A, 108A, 110A, 112A.

The retaining means comprise means for returning the actuation button 88. The means for returning the actuation button 88 may comprise a spring, such as a return spring 114 working for example in compression. Alternatively, the return spring may work in traction.

The retaining means also comprise a pad 116, the return means 114 being arranged between the actuation button 88 and the pad 116.

Figure 11:
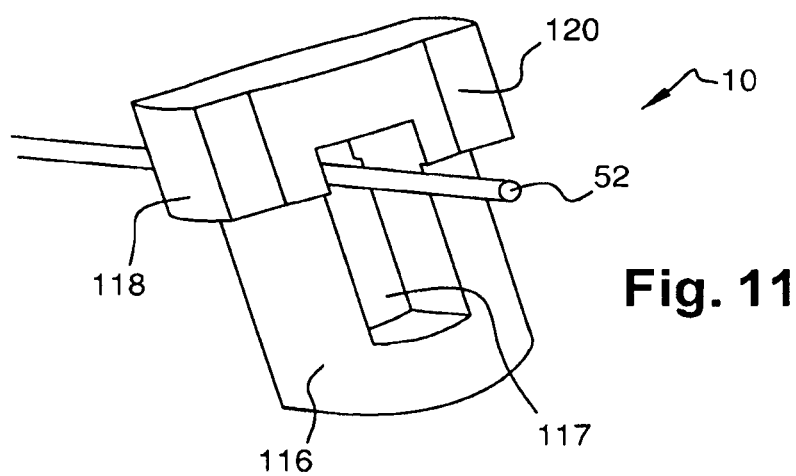
FIG. 11 is a perspective view of another detail of the implant injection device of FIG. 1.

In this case, the pad 116 is attached to the unit 11 and comprises a hole 117 for the pushing rod 52 to go through (shown on FIG. 11). It further comprises protrusions 118, 120 shown on FIG. 11 and cooperating with grooves 122, 124 formed in the actuation button 88 and shown respectively on FIGS. 2bis and 6. In this case therefore, the actuation button 88 can only move in translation along the grooves 122, 124 in a direction substantially orthogonal to the injection direction, over a stroke limited by lower and upper stops of the grooves 122, 124.

In the example shown, the actuation button 88 is slidably mounted in the unit 11, in a direction substantially orthogonal to the injection direction. Alternatively, the actuation button 88 may be a lateral actuation button pivotally mounted about an axis substantially orthogonal to the injection axis.

Lastly, the retaining means may comprise a support ramp formed on the actuation button 88, the unit 11 or the pad 116. Thus, when the user presses the actuation button 88, the retaining force exerted by the support ramp on the pushing rod 52 decreases, allowing the displacement of the pushing rod 52. A support ramp may mean in particular a substantially flat surface, inclined relative to the plane defined by the injection direction and the direction of the return force exerted by the return spring 114, whose intersection with this plane defines an axis substantially parallel to the injection direction.

In the example shown, the retaining means are continuously adjustable. Thus, the speed of displacement of the pushing rod 52 under the action of the pushing means, in particular the thrust spring 70, can be varied manually. A user can in fact actuate the actuation button 88 by pressing with a variable force. If the pressing force increases, the second retaining forces decrease and the speed of displacement of the pushing rod 52 increases. In particular, at least one retaining force can be zero. On the contrary, if the pressing force decreases, the frictional forces increase, so the second retaining forces increase and the speed of displacement of the pushing rod 52 decreases.

The retaining means comprise a pad, carried by the unit 11 as shown on FIGS. 12 to 15. The pad may consist of the pad 116. It comprises a third bearing surface 116A, intended to be in contact with the pushing rod 52 to create an additional retaining force on the pushing rod 52, in particular when the retaining means are not actuated by the user. Alternatively, the pad 116 may form the bearing support 110, 112 comprising the third bearing surface 116A intended to be in contact with the pushing rod 52. In this case, the guide holes 110, 112 may not form the second bearing surface 110A, 112A, the second bearing surface being formed in this case by the third bearing surface 116A.

Figure 12:
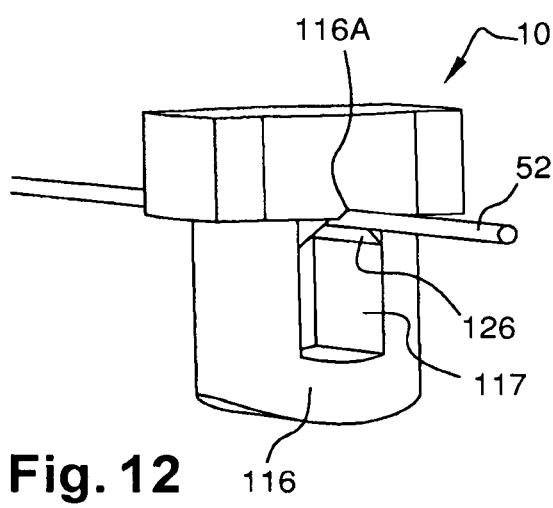
FIG. 12 is a perspective view of a detail of an implant injection device according to a second embodiment.

In the example shown on FIGS. 12 and 14, the pad 116 comprises a hole 117 of special shape for the pushing rod 52 to go through. The shape of the upper part of the hole 117 is complementary to that of the pushing rod 52, in other words partially cylindrical, so as to increase the contact area between the pushing rod 52 and the wall of the upper part of the hole 117 to form the third bearing surface 116A. Thus, the additional retaining force can be increased by the frictional forces present on the third bearing surface 116A. The hole 117 may also comprise guide walls 126 for guiding the pushing rod 52 towards the third bearing surface 116A, for example V-shaped.

Figure 13:
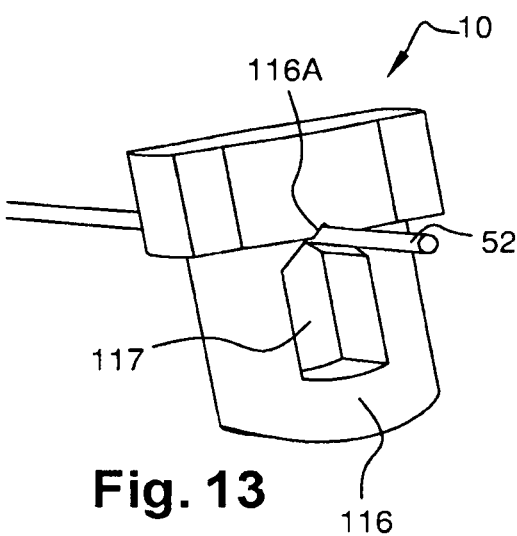
FIG. 13 is a perspective view of a detail of an implant injection device according to a third embodiment.
Figure 15:
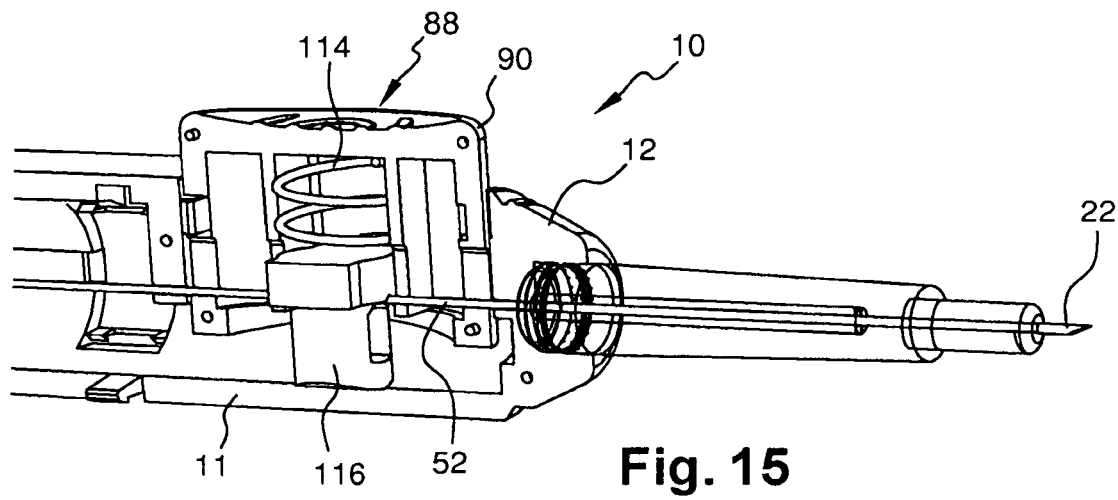
FIG. 15 is a perspective view of a part of the implant injection device of FIG. 13.

The pad 116 shown as an example on FIGS. 13 and 15 is different from that shown on FIGS. 12 and 14 in that the upper part of the hole 117 is formed by the extension of the V-shaped guide walls 126. Thus, the third bearing surface 116A between the pushing rod 52 and the wall of the upper part of the hole 117 is formed substantially by two straight longitudinal contact areas.

At least one from the first bearing surface 102A, 104A, 106A, 108A, the second bearing surface 110A, 112A and, where applicable, the third bearing surface 116A has a high coefficient of static friction with the pushing rod 52, for example greater than 0.5. In particular, the first bearing surface 102A, 104A, 106A, 108A and/or the third bearing surface 116A has a high coefficient of static friction with the pushing rod 52, for example greater than 0.5. In the remainder of the document, the term bearing surface will be used for the first, second and third bearing surfaces 102A, 104A, 106A, 108A, 110A, 112A, 116A.

Thus, the characteristics of friction between the two surfaces are generally described by two coefficients of friction: static $\mu_s$ and dynamic $\mu_k$.

The main parameters involved are:
the force exerted by the bearing surface considered on the pushing rod 52, which depends on the contact pressure. The contact pressure depends in particular on the length of contact between the bearing surface and the pushing rod 52, for example greater than or equal to 25 mm, and on the diameter of the pushing rod 52, for example less than or equal to 1 mm;
the materials of each surface in contact: considering that the pushing rod 52 is made of steel, and that the material of at least one bearing surface, for example the material of the pad 116, is a frictional plastic material, the surfaces in contact may have a high static coefficient of friction, typically greater than 0.5.

A frictional plastic material may include at least one of the materials chosen from the following list: unloaded polymers having a low degree of crystallinity and generally having a glass transition temperature less than ambient temperature; thermoplastic elastomers, such as TPE, TPU; thermosetting elastomers such as natural gums, having for example a glass transition temperature of −70° C., polyurethane; silicones. Moreover, the addition of rubber nodules and/or other loads to a polymer material also increases the coefficient of friction, which extends the choice of the base-forming polymer material.

The thrust spring 70 and the return spring 114 may be made of metal, for example stainless steel.

The other elements of the implant injection device 10, whose material is not specified in this description, may be made of a thermoplastic material, for example polyethylene or polypropylene.

An example of operation of the implant injection device 10 will now be described.

The implant injection device 10 as shown on FIG. 1 is in storage configuration before use.

The user must remove the cap 16, as shown on FIG. 2—the implant injection device 10 being considered to be assembled—and check that the one or more implants 26, 28 are present by looking through the receiver housing 24.

The user can then remove the key 76. At this stage, the pushing rod 52 is subjected to the action of the thrust spring. However, the pushing rod 52 is stationary and is not displaced under the action of the thrust spring 70, due to the frictional retaining means, which exert the first retaining forces on the pushing rod 52. In particular, the pushing rod 52 is retained by the retaining forces exerted by the first bearing surfaces 102A, 104A, 106A, 108A formed by the grooves 102, 104, 106, 108, and by the second bearing surfaces 110A, 112A formed by the guide holes 110, 112 and/or by a pad 116.

Figure 8:
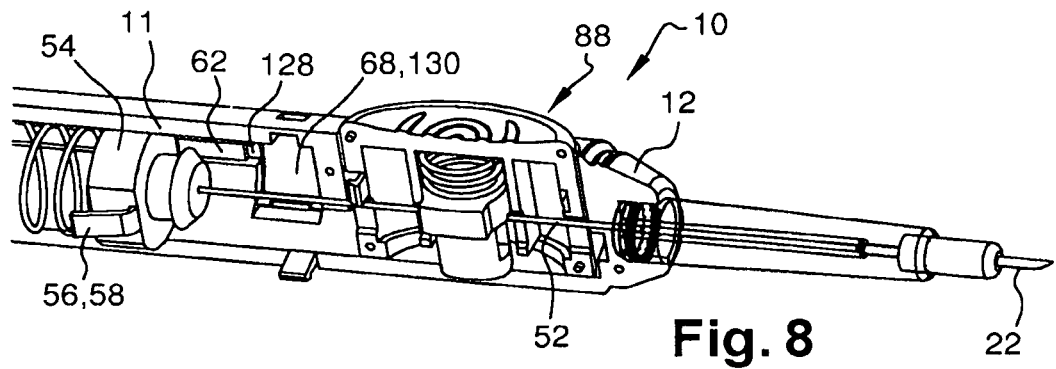
FIG. 8 is an enlarged view of a part of FIG. 3.

As shown on FIGS. 3 and 8, the key 76 being removed, the injection needle 22 is then inserted into the patient's body and the user presses the actuation button 88 to release the displacement of the pushing rod 52. This causes the displacement of the pushing rod 52 under the action of the thrust spring 70, said pushing rod pushes an implant, in particular the first implant 26, into the patient's body. Thus, on FIG. 3, the pushing rod is shown in the intermediate position, which corresponds in the example shown to the injection of a first implant 26 into the patient's body, a second implant 28 remaining in the injection needle 22. As described previously, the speed of displacement of the pushing rod 52 can be varied, or the displacement of the pushing rod 52 can even be stopped under the action of the frictional retaining means. This may be desirable, for example, between each implant injection, if the implant injection device 10 is used to inject several implants 26, 28, since in this case the direction of the injection needle 22 and therefore the injection direction relative to the skin can be modified so that the two implants 26, 28 can be injected in parallel in two different directions, and not in series, to limit the depth of injection of the implants 26, 28. This may also be desirable if the user wants to move the implant injection device 10 after injecting a first implant 26 to start from another injection point to inject a second implant 28.

Figure 4:
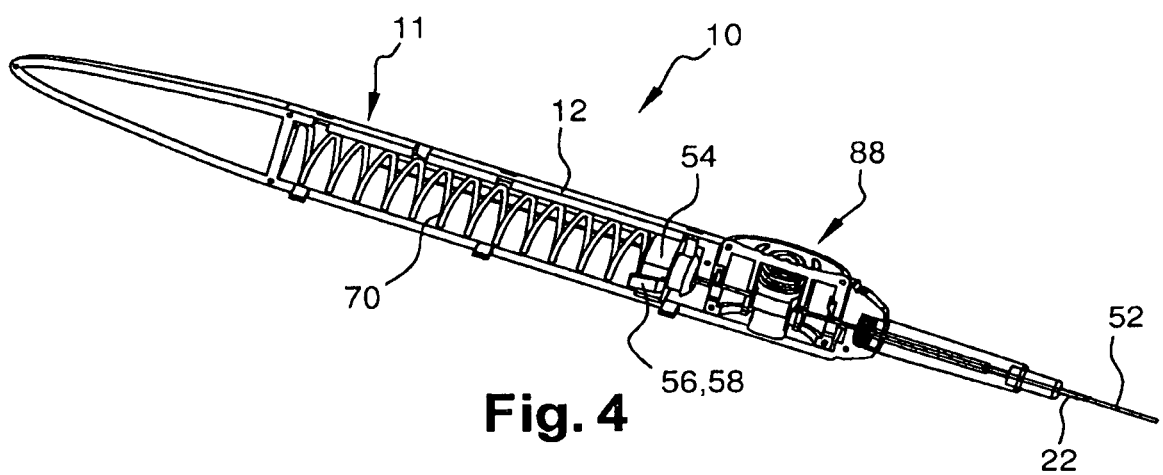
FIG. 4 is a view similar to FIG. 2, the pushing rod being in a final position.
Figure 9:
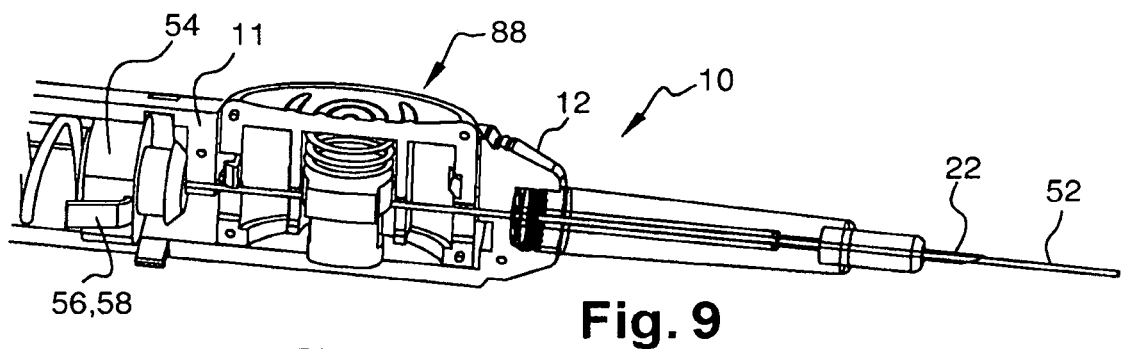
FIG. 9 is an enlarged view of a part of FIG. 4.

FIGS. 4 and 9 show the implant injection device 10 in the final position of the pushing rod 52. In this final position, the pushing rod 52 projects towards the distal direction past the end 30 of the injection needle 22. Still in this final position, the control element 54 is in abutment against an abutment surface of the unit 11. In addition, the implant injection device 10 comprises locking means arranged to block the pushing rod 52 in the final position. Thus, in this final position, the lug 56, 58 of the control element 54 cooperates with a recess 128 carried by the unit 11, formed in particular in the unit 11 at the end of the groove 60, 62 towards the distal direction, said recess being shown on FIG. 8. Advantageously, the movement of the lug 56, 58 from the groove 60, 62 to the recess 128 generates an audible signal such as a "click" that can be heard by the user.

The stroke of the pushing rod 52 between the initial position and the final position may, for example, extend over a length from 10 to 50 mm, in particular between 30 and 40 mm, preferably configured to inject two implants 26, 28 each having a length close to 8 mm.

An example of assembly of the implant injection device 10 will now be described.

Firstly, a cover 68 is assembled in each half-unit 12, 14 by clipping brackets 69 on the respective half-unit 12, 14. The thrust spring 70 is then arranged in the half-unit 12 against the inner stop 72. The thrust spring 70 is compressed and the control element 54 is arranged in the half-unit 12 against the thrust spring 70. The control element 54 is then moved into a position allowing the key 76 to be inserted in the orifice 78 and the control element 54 to be held in position by the key 76 by the engagement of the branches 82, 84 of the key 76 in the peripheral groove 86 of the control element 54. Then, the half-button 90 and the pad 116 are arranged in the half-unit 12. The return spring 114 is then placed between the half-button 90 and the pad 116. The pushing rod is now inserted through the hole 117 of the pad 116 of the actuation button 88 and is engaged in the control element 54 so as to be attached to the control element 54. The half-button 92 is then attached to the half-button 90 so as to form the actuation button 88. The half-unit 14 equipped with the cover 68 is then attached to the half-unit 12 equipped with the above-mentioned elements.

Independently of this, the injection needle 22 can be equipped with the support element 32. In particular, the support element 32 is overmoulded on the injection needle 22. Alternatively, the support element 32 can be forcibly engaged on the injection needle 22 to obtain a tight fitting between the support element 32 and the injection needle. The receiver housing 24 is then tightly fitted or overmoulded on the assembly thus produced. The receiving member 40, housing the implants 26, 28 is then inserted into the receiver housing 24 in the bore 38.

Lastly, the assembly formed by the injection needle 22, the protective housing 24, the support element 32, the receiving member 40 and the implants 26, 28 is assembled on the unit 11 in the bore 48, by clipping the peripheral clipping groove 44 of the protective housing 24 on the peripheral protrusion 46 of the unit 11. Note that this last step may possibly be carried out subsequently, for example by the user.

The invention is not limited to the embodiments described and other embodiments will be clearly apparent to those skilled in the art.

In particular, the user and the patient may be the same person. Although the implant injection device 10 is shown in particular with two implants 26, 28, the implant injection device 10 may be configured to inject a single, very long implant. Alternatively, the implant injection device 10 may be configured to inject a plurality of implants in the form of hollow balls or spheres containing a product, for example between 2 and 50 implants, more precisely between 10 and 20 implants.

The invention claimed is:

1. An implant injection device, comprising:
   an injection needle,
   a receiver housing for receiving at least one implant,
   an injection device, comprising:
      a pushing rod configured to be arranged upstream from the at least one implant housed in the receiver housing and configured to push the at least one implant through the injection needle between an initial position of the at least one implant and a final position of the at least one implant,
      a pushing member for pushing the pushing rod between an initial position of the pushing rod, wherein the at least one implant is in the initial position of the at least one implant, and a final position of the pushing rod, wherein the at least one implant is in the final position of the at least one implant,
      a retaining member for retaining the pushing rod by friction relative to the injection needle, opposing a displacement of the pushing rod to the final position of the pushing rod, the retaining member being continuously adjustable to vary manually a displacement speed of the pushing rod under a force applied from the pushing member,
   wherein the retaining member comprises:
      an actuation button comprising a first bearing surface configured to be in direct contact with the pushing rod, and
      a bearing support comprising a second bearing surface configured to be in direct contact with the pushing rod,
   wherein the actuation button is movable relative to the bearing support between a retaining position, in which the first and second bearing surfaces exert a first retaining force on the pushing rod, and a release position, in which the first and second bearing surfaces exert a second retaining force less than the first retaining force on
   the pushing rod, the second retaining force allowing a displacement of the pushing rod towards a distal direction relative to the injection needle.

2. The implant injection device according to claim 1, wherein the retaining member comprises a return spring for returning the actuation button to its retaining position.

3. The implant injection device according to claim 1, comprising a control element for controlling the pushing rod, slidably mounted relative to a unit, the unit and the control element being provided with a guide for guiding in translation the control element relative to the unit.

4. The implant injection device according to claim 1, wherein the pushing member comprises a thrust spring resting between a unit and the pushing rod.

5. The implant injection device according to claim 1, comprising a retractable locking element for blocking the pushing member, configured
   in a locking configuration, to hold the pushing rod in the initial position of the pushing rod,
   in a retracted configuration, to allow the pushing rod to move to the final position of the pushing rod.

6. The implant injection device according to claim 1, comprising a locking member arranged to block the pushing rod in the final position of the pushing rod.

7. The implant injection device according to claim 6, wherein in the final position of the pushing rod, the pushing rod projects towards a distal direction past an end of the injection needle.

8. The implant injection device according to claim 1, wherein the retaining member comprises a pad carried by a unit, comprising a third bearing surface intended to be in contact with the pushing rod to create an additional retaining force on the pushing rod.

* * * * *